United States Patent [19]

Dewey, Jr. et al.

[11] 4,051,371

[45] Sept. 27, 1977

[54] OPTO-ACOUSTIC SPECTROSCOPY EMPLOYING AMPLITUDE AND WAVELENGTH MODULATION

[75] Inventors: C. Forbes Dewey, Jr., Belmont; Lon O. Hocker, Newton, both of Mass.

[73] Assignee: Massachusetts Institute of Technology, Cambridge, Mass.

[21] Appl. No.: 680,622

[22] Filed: Apr. 26, 1976

[51] Int. Cl.$^2$ .............................................. G01N 21/26

[52] U.S. Cl. ...................................... 250/339; 250/343

[58] Field of Search ............... 250/343, 345, 351, 339; 356/206, 97, 85

[56] References Cited

U.S. PATENT DOCUMENTS

| | | | |
|---|---|---|---|
| 3,700,890 | 10/1972 | Kruezer | 250/343 |
| 3,820,901 | 8/1974 | Kruezer | 250/345 |
| 3,884,583 | 5/1975 | Kikuchi | 356/85 |

*Primary Examiner*—Alfred E. Smith
*Assistant Examiner*—B. C. Anderson
*Attorney, Agent, or Firm*—Arthur A. Smith, Jr.; Robert Shaw; Charles Hieken

[57] ABSTRACT

An intense light source, preferably of high monochromaticity, having its beam modulated at a frequency $f_o$ through a wavelength range including an absorption line of a species to be detected, energizes a chamber containing a sample of the species. The modulation frequency may also be a multiple or sub-multiple of the natural resonant accoustic frequency of the sample chamber. A microphone in the sample chamber provides an output signal proportional to the concentration of the species. The radiation beam is further incident upon a calibration chamber containing a predetermined concentration of the species. A microphone in the calibration chamber provides a calibration signal for comparison with the sample signal to determine the concentration of the species in the sample cell. Means are provided for adjusting the center of the wavelength modulation range so that it bears a known relation to the center of the species absorption line.

16 Claims, 6 Drawing Figures

OPTO-ACOUSTIC SPECTROSCOPY EMPLOYING AMPLITUDE AND WAVELENGTH MODULATION

The Government has rights in this invention pursuant to Contract Nos. DAHCO4-71-C-0049 and N00014-67-A-0204-0092 awarded respectively by the Department of the Army, Advanced Research Projects Agency and the Office of Naval Research of the United States Navy.

BACKGROUND OF THE INVENTION

The present invention relates in general to detecting the character of a medium in a sample chamber using acoustic signals produced by absorption of radiation; and more particularly concerns novel apparatus and techniques for detecting atmospheric pollutants using acoustic signals produced by absorption of wavelength-modulated radiation to achieve exceptionally high isolation of system error and noise, thereby facilitating detection.

It is known to measure trace gaseous constituents using acoustic signals produced by absorption of infrared radiation. In this technique the absorbed radiation heats the gas, inducing an acoustic wave which is detected by a suitable detector. The strength of the acoustic wave is directly related to the amount of radiation absorbed by the sample being analyzed. A method originally described by Bell, Tyndall, and others in the 19th Century was improved by L. B. Kreuzer, U.S. Pat. No. 3,700,890. A different method, where the incident radiation source is modulated at an acoustic resonant frequency of the chamber containing the sample to be analyzed, is described in Appl. Phys. Letters, 23, 633 (1973). Further elaborations of the art have used wavelength-modulated lasers to perform derivative spectroscopy, as exemplified by the paper of Hinkley and Sample, Applied Optics, 14, 859 (1975). A theoretical description is given by Sulzmann et al., *Combustion and Flame*, 20, 177 (1973). Still other art has used wavelength modulation of the optical source in a nonresonant spectrophone, e.g. C.K.N. Patel writing in *Coherence and Quantum Optics*, Plenum Press, N.Y., 1973, pp. 567–593.

To varying degrees, prior art opto-acoustic spectroscopy systems discussed above are susceptible to certain inaccuracies. For example, they are not self-calibrating; that is, there is no intrinsic method of insuring the relation between absorbed power and acoustic signal. If the radiation source wavelength is not fixed, no method is available to insure that the radiation wavelength is tuned to the correct value for the desired measurement. No method is available for detecting the fraction of the acoustic signal which arises from unwanted sources, such as the absorption of the sample chamber windows and absorption and spurious scattering from aerosols and the like.

Accordingly, it is an important object of the invention to provide an opto-acoustic spectroscopy system that overcomes one or more of the disadvantages set forth above.

It is another object of the invention to achieve the preceding object with an opto-acoustic spectroscopy system that discriminates against signals arising from unwanted sources.

It is a further object of the invention to achieve one or more of the preceding objects with an opto-acoustic spectroscopy system that is self-calibrating.

It is another object of the invention to achieve one or more of the preceding objects with an opto-acoustic spectroscopy system having the radiation wavelength tuned to the correct value for the desired measurement.

It is a further object of the invention to achieve one or more of the preceeding objects by utilizing a wavelength modulation frequency which is a multiple or sub-multiple of a resonant acoustic mode of the chamber containing the gas sample being measured.

SUMMARY OF THE INVENTION

According to the invention there is sample chamber means for receiving a medium having components to be detected. A source of a beam of substantially monochromatic radiant energy modulated through a wavelength range embracing spectral lines characteristic of the component to be detected energizes the sample chamber. Modulation of the source wavelength produces pressure fluctuations within the chamber with spectral components at the modulation frequency and at harmonics of the modulation frequency. Means may be provided for modulating the intensity of the radiant energy beam to facilitate detection of absorbed radiation and discriminate against sources of signal noise. Acoustic detecting means detects the pressure wave within the sample chamber to provide a plurality of output signals representative of the intensity of the spectral components of the pressure wave caused by energy being absorbed in the sample chamber. The radiant energy beam may also energize a calibration chamber having a predetermined known absorption characteristic to provide an output calibration signal for calibrating the electronic apparatus coupled to the output of the sample chamber means.

Numerous other features, objects and advantages of the invention will become apparent from the following specification when read in connection with the accompanying drawing in which:

DETAILED DESCRIPTION OF PREFERRED EMBODIMENTS

Figure 1:
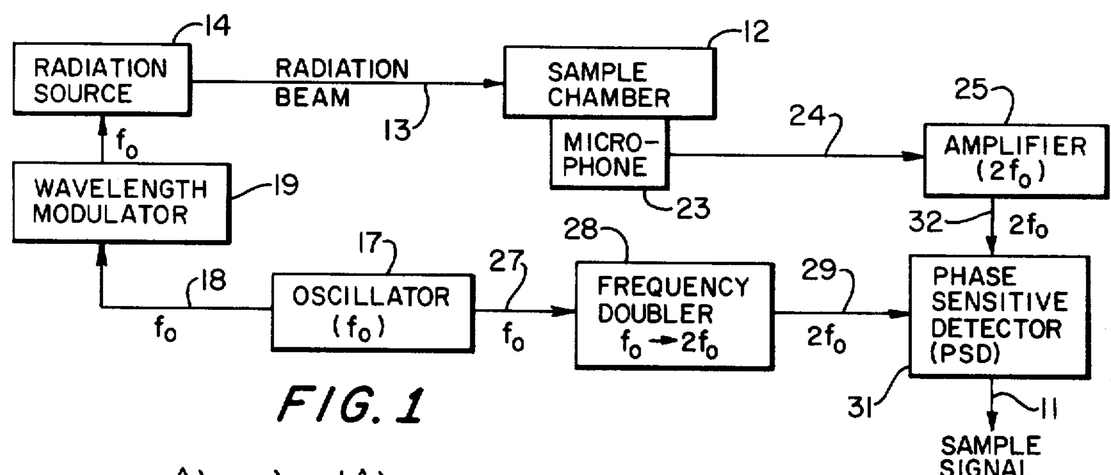
FIG. 1 is a block diagram illustrating the logical arrangement of a system according to the invention.

Referring to FIG. 1 there is shown a block diagram illustrating the logical arrangement of a system according to the invention. The sample signal on output line 11 is representative of the degree of absorption by the medium then in sample chamber 12 of the energy from radiation beam 13 provided by the radiation source 14. Corresponding elements are identified by the same reference symbol throughout the drawing.

Oscillator 17 provides a modulating signal of frequency $f_o$ on line 18 to modulator 19 that modulates the wavelength of radiation source 14, typically a wavelength tunable laser, through a wavelength range embracing the spectrum characteristic of the component or species to be detected. Radiation beam 13 is incident upon sample chamber 12 to produce a pressure wave in the sample chamber which is detected by the microphone 23 to provide a corresponding electrical signal on line 24 which is amplified by amplifier 25. Oscillator 17 provides a signal of frequency $f_o$ on line 27 to frequency multiplier 28 to produce reference signals at frequencies $2f_o$, $3f_o$, $4f_o$, . . . on line 29 to phase sensitive detector 31 for comparison with the amplified signal on line 32 to provide the sample signal on output line 11.

Figure 2:
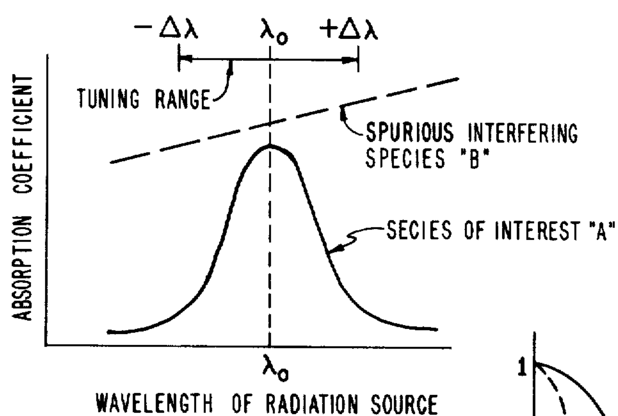
FIG. 2 is a graphical representation of absorption coefficient as a function of wavelength for a species to be detected and a spurious interfering species.

Referring to FIG. 2 there is shown a graphical representation of absorption coefficient as a function of wavelength for a species to be detected and a spurious interfering species over a range embraced by the wavelength range swept by radiation source 14. For purpose of illustration, the wavelength tuning range is shown as being centered on the peak of the absorption line of species A; while this is a preferred condition, it is not necessary to the successful employment of this invention. As the wavelength of radiation beam 13 sweeps through a range from $(\lambda_o - \Delta\lambda)$ to $(\lambda_o + \Delta\lambda)$, it passes through the absorption spectrum of species of interest "A" centered at $\lambda_o$ and that of the interfering species B. The radiation beam 13 excites the absorption spectra twice each cycle to produce a characterizing pressure wave of species in the chamber having a maximum at a frequency of $2f_o$.

If the intensity of radiation beam 13 is substantially constant, the pressure wave signal component characteristic of spurious species B is predominantly of frequency $f_o$ with a negligible component at frequency $2f_o$. It is thus possible to discriminate against signals produced by spurious species B and enhance the signal arising from species of interest A by measuring the microphone response in a frequency band near $2f_o$. This effect is more particularly described in the following paragraphs.

A useful approximate relation describing the absorption coefficient of a spectral line of gaseous species A is the Lorentz formula [with $\nu \equiv \lambda^{-1}$, $cm^{-1}$]

$$\sigma = \sigma_o \left[ 1 + \left( \frac{\bar{\nu}}{\gamma} \right)^2 \right]^{-1} \quad (1)$$

where $\sigma$ is the absorption coefficient ($cm^{-1}\,atm^{-1}$), $\sigma_o$ is the absorption coefficient at the line center, $\bar{\nu} \equiv (\nu - \nu_o)$ is the difference between the incident radiation wavelength, $\nu$ ($cm^{-1}$), and the line center, $\nu_o$ ($cm^{-1}$), and $\gamma$ is the half-width of the line ($cm^{-1}$). For illustrating the novel features of this invention, we assume that the wavelength of the incident radiation is modulated sinusoidally according to $$\nu = \nu_a + \epsilon \sin \omega t \quad (2)$$

where the modulation frequency, $f_o$, is equal to $\omega/2\pi$. Thus, $\nu = (\nu_a - \nu_o) + \epsilon \sin \omega t$ and Eq. (1) may be written $$\sigma/\sigma_* = [1 + a_1 \sin \omega t + a_2 \sin^2 \omega t]^{-1} \quad (3)$$

where $$\left.\begin{array}{ll} a_1 = \dfrac{2bc}{1+c^2} & b = \dfrac{\epsilon}{\gamma} \\ a_2 = \dfrac{b^2}{1+c^2} & c = (\nu_a - \nu_o)/\gamma \\ \sigma_* = \dfrac{\sigma_o}{1+c^2} & \end{array}\right\} \quad (4)$$

The term $b$ is a measure of the magnitude of wavelength modulation, and $c$ is a measure of the displacement of the central wavelength, $\nu_a$, of the incident radiation from the center of the absorption line, $\nu_o$.

A preferred operating condition is when the incident radiation is modulated in wavelength about the absorption line center. Then $c = 0$, and $$\sigma/\sigma_* = (\sigma/\sigma_o)\,[1 + b^2 \sin^2 \omega t]^{-1} \quad (5)$$

Figure 3:
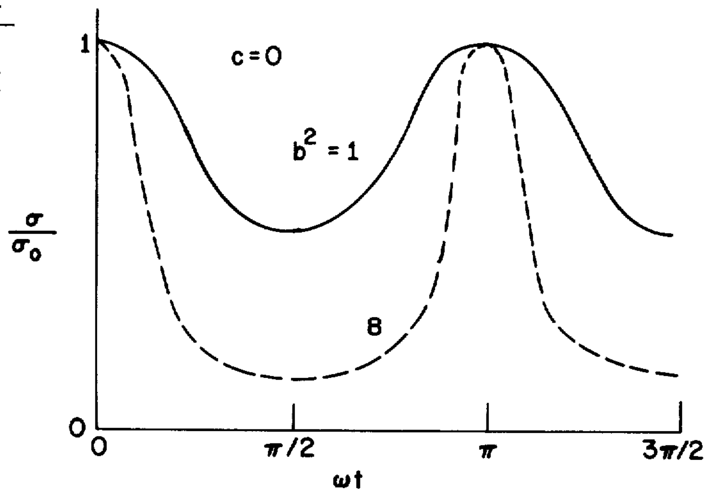
FIG. 3 is graphical representation of normalized absorption coefficient as a function of $\omega t$.

The absorption coefficient $\sigma$, which is proportional to the power absorbed by species A and to the acoustic signal received by the microphone 23, varies with time and the parameter $b^2$ as illustrated in FIG. 3. By inspection of the Figure, it is clear that, for $c = 0$, there is a substantial component of the microphone signal at twice the modulation frequency. By techniques of Fourier analysis, it is possible to calculate the harmonic content of the microphone signal; thus, for example, for $b = 1$ the ratios of successive terms of the Fourier analysis (representing the relative magnitudes of signals received by the microphone 23) are:

| Steady Component | : | 1st Harmonic at $f_o$ | : | 2nd Harmonic at $2f_o$ | : | 3rd Harmonic at $3f_o$ | : | 4th Harmonic at $4f_o$ |
|---|---|---|---|---|---|---|---|---|
| 1 | : | 0 | : | 0.242 | : | 0 | : | 0.057 |

It is a general result that the intensity of the microphone signal at $f_o$ and all odd harmonics ($3f_o$, $5f_o$, . . . ) are zero for $c = 0$.

Opto-acoustic detectors of prior art have been plagued by signals arising from scattering and absorption by aerosols, and absorption by optical windows. Generally these sources of absorption are characterized by the relation $\sigma(\nu)$ = constant. Therefore, in the present invention such sources would not yield any signal at either frequency $f_o$ or $2f_o$.

It is useful to compare the method of detection of this invention with prior art as typified by the publication of Hinkley and Sample and that of Patel mentioned previously. These methods utilize very small modulation of the wavelength of excitation. In the present terminology, this corresponds to $b << 1$ and from Eq. (3) and (4) we find the largest terms to be $$\frac{\sigma}{\sigma_*} = \frac{1}{1 + \left(\dfrac{2bc}{1+c^2}\right)\sin \omega t} \approx 1 - \left(\frac{2bc}{1+c^2}\right)\sin \omega t \quad (6)$$

Eq. (6) demonstrates that prior art produces a signal with the major contribution to the fluctuating microphone signal at the modulation frequency $f_o$. This signal decreases as $c^{-1}$ for large $c$, is zero at the center of the absorption line, and shows a maximum at $c = 1$.

It is the signal at $f_o$ which has been employed by the prior art of derivative spectroscopy to detect the presence of Species A (see, e.g., the references cited previously and the numerous works cited therein). While this method of detection using frequency $f_o$ is successful in discriminating against interfering acoustic sources B such as aerosols and sample chamber windows and the like for which $\sigma$ is independent of excitation wavelength, the present invention offers substantial, and hitherto unexploited, advantages on discriminating against interference by species B for which $\sigma$ is not constant.

These advantages are illustrated by the typical case where species B has a very strong absorption line near the measurement line of species A at $\nu_o$ (see FIG. 2). This situation is encountered frequently in measuring atmospheric pollutants in the presence of normal atmospheric constituents such as $CO_2$ and water vapor, as described by Gelbwach, *Applied Optics*, 13, 1005 (1974) and others. The center of the absorption line of the interferor B is typically displaced from $\nu_o$ such that $c >> 1$, and the absorption coefficient modulation in time for species B is $$\sigma_{B^*}/\sigma_{B^*} \approx 1/[1 + \beta \sin \omega t]^2 \tag{7}$$

where $\beta = \epsilon/(\nu_B - \nu_o)$ and $\beta$ is small. A Fourier analysis of Eq. (7) for $\beta << 1$ gives $$\sigma_B/\sigma_{B^*} = 1 - 2\beta \sin \omega t - (3/2)\, \beta^2 \cos 2\, \omega t - \beta^3 \sin 3\, \omega t + \ldots \tag{8}$$

Eq. (8) shows that the interferor B produces microphone signals in the ratios:

| Steady Component | : | 1st Harmonic at $f_o$ | : | 2nd Harmonic at $2f_o$ | : | 3rd Harmonic at $3f_o$ |
|---|---|---|---|---|---|---|
| 1 | : | $2\beta$ | : | $3/2\ \beta^2$ | : | $\beta^3$ |

Typical values of $\beta$ encountered in practice will range from 0.1 to 0.01. It is seen, therefore, that the interferor B produces a much larger signal at frequency $f_o$ than at frequency $2f_o$. By employing the present invention whereby signals are detected at $2f_o$, the unwanted signal produced by species B is minimized with respect to the desired signal arising from species A.

A detailed examination of Eq. (3) demonstrates that the rejection of unwanted signals from species B depends strongly upon the detailed shapes of the absorbing lines of species A and species B. In certain instances, it may prove desireable to employ detection schemes in which the desired signal is at a frequency $f_o$ whereas the interfering species contain substantial harmonic content only at higher frequencies. A case in point is detection of the toxic compound Nickel carbonyl. This heavy molecule has a very broad absorption line relative to the very narrow absorption lines of interfering species. By employing very large wavelength modulation of the beam, such that $\epsilon$ is large compared to the linewidths of the interfering species, the dominant signal contributions of the interfering species will appear at much higher frequencies and detection of the desired signal may be accomplished at either $f_o$ or $2f_o$, depending upon the value of $c$ and the nature of the interfering species.

The present method provides additional information in the magnitudes of the signals produced at $f_o$, $2f_o$, $3f_o$, . . . which may be used to correct for background signals arising from the interfering species B. As an example, consider the case where the wavelength modulation is centered at $\nu_o$, i.e. $c = 0$. Then the signal at $2f_o$ contains two components, one proportional to $0.242\sigma_*$ and the other proportional to $(3/2)\, \beta^2 \sigma_{B^*}$. At $f_o$ and $3f_o$, only signals from the interferor B are present. Therefore, for $\beta << 1$, from Eq. (8), the magnitude ratio $$S = \frac{\text{Signal at } 3f_o}{\text{Signal at } f_o} = \frac{\beta^2}{2} \tag{9}$$

and the magnitude of $\beta$ may be determined from the measured ratio S as $$\beta = (2S)^{1/2} \tag{10}$$

Therefore, one may calculate the unwanted signal component at $2f_o$ introduced by species B to be proportional to $3S\ \sigma_{B^*}$, and the signal at $2f_o$ arising from response to species A may be calculated by $$T = \frac{\text{Signal at } 2f_o \text{ from A}}{\text{Total signal at } 2f_o} = \frac{0.242\sigma_*}{0.242\sigma_* - 3S\sigma_{B^*}} \tag{11}$$

where the minus sign in the denominator indicates that the contributions from species A and B are out of phase. The magnitude of the absorption coefficient $\sigma_{B^*}$ may be determined in terms of $\sigma_*$ (which is known from calibration) by utilizing the measured ratio of signals at $f_o$ and $2f_o$:

$$U = \frac{\text{Signal at } 2f_o}{\text{Signal at } f_o} = \frac{0.242\sigma_* - 3S\sigma_{B^*}}{-2\sqrt{2S}\ \sigma_{B^*}} \tag{12}$$

or $$\frac{\sigma_*}{\sigma_{B^*}} = \frac{2\sqrt{2S}}{0.242}\left[-U + \frac{3}{2\sqrt{2}}\, S^{1/2}\right] \tag{13}$$

The desired signal ratio, T, is then $$T = 1 - \frac{3}{2\sqrt{2}}\, \frac{S^{1/2}}{U} \tag{14}$$

We have shown, therefore, that the information contained in the measured signals at $f_o$, $2f_o$, and $3f_o$ may be used to determine the amount of signal at $2f_o$ which is present because of an interfering species B. This allows the desired signal at $2f_o$ arising from species A to be computed more accurately than hitherto possible.

The method of producing acoustic signals at $2f_o$ as described herein may be contrasted with the production of signals at $2f_o$ as described in the aforementioned patent to Kreuzer. In the Kreuzer patent, the signal at $2f_o$ is specifically related to the amplitude modulation of the radiation beam at frequency $f_o$, whereas in the present instance the signal at $2f_o$ is achieved by wavelength modulation, even with a constant intensity beam. Furthermore, the secondharmonic signal of Kreuzer requires that the source intensity be sufficiently strong to excite a substantial fraction of the molecules being detected in the sample chamber. No such restriction exists in the method of the present invention.

Prior art, as represented by the publication of Dewey et al, *Appl. Phys. Lett.*, 23, 633 (1973), teaches that it may be desirable to amplitude modulate the radiation beam at a frequency corresponding to a natural acoustic resonance mode of the sample chamber. The acoustic resonance mode is useful in combination with the wavelength modulation system discussed above. If $f_r$ represents the frequency of acoustic resonance, then resonance can be achieved by adjusting the wavelength modulation frequency such that $f_r = 2f_o$.

Figure 5:
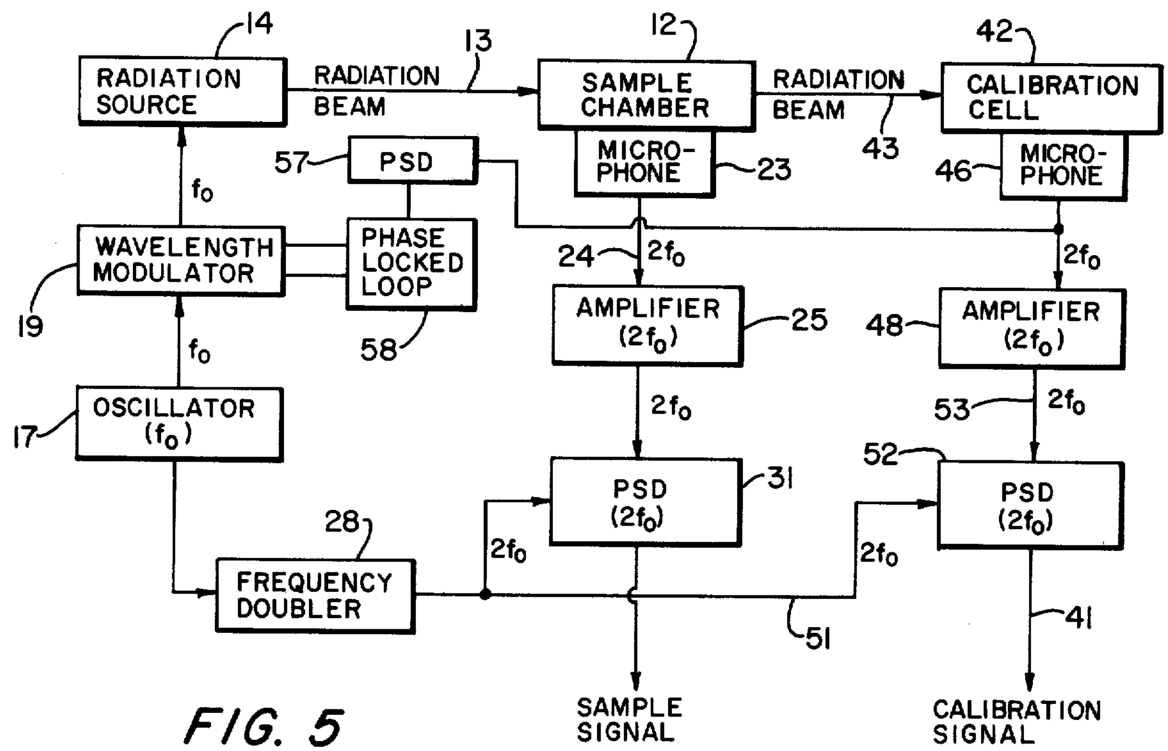

It is also within the scope of this invention to employ both amplitude and wavelength modulation. Referring to FIG. 5 there is shown a block diagram illustrating the logical arrangement of a system according to the invention which includes both amplitude and wavelength modulation. Wavelength modulator 19, oscillator 17, frequency doubler 28, and microphone 23, operate as in the system discussed above in reference to FIG. 1. A second oscillator 61 at frequency $f_r$ corresponding to a resonance of sample chamber 12, provides a modulating signal to amplitude modulator 62 which modulates the amplitude of radiation beam 13 incident upon sample chamber 12 to produce pressure waves within the sample chamber of frequency $f_r$ which are superimposed upon the pressure waves at $2f_o$. Oscillator 61 also provides a reference signal to phase sensitive detector 66 for comparison with the amplified signal on line 67 of frequency $f_r$. The output signal on line 66 from phase sensitive detector 66 is modulated at frequency $2f_o$ and this signal 28 is applied to phase sensitive detector 31 for comparison with the reference signal provided by doubler 28 to provide the sample signal on line 11.

Preferably the two frequencies, $f_r$ and $f_o$, differ substantially. If $f_r$ is made resonant at the lowest-order radial acoustic mode of a 2 cm diameter cylindrical chamber and air is used as the primary gas in the chamber, the frequency $f_r$ would typically be about 20 KHz. Such a chamber would have an acoustic response time to changes in absorption equal to $f_r^{-1}$ times the acoustic gain, Q, of the cell. For example, with a valve Q of 500 and $f_r = 20$ KHz, the response time would be (1/40) sec. To achieve full benefit from wavelength modulation in this system, it is desirable that the wavelength modulation frequency $f_o$, be smaller than one-half the inverse of the acoustic response time.

The fraction of incident radiation absorbed by the sample chamber is often small. A calibration chamber that is preferably similar to the sample chamber may then be placed in series with the sample chamber. Referring to FIG. 5, there is shown a block diagram illustrating the logical arrangement of a system according to the invention which includes a series calibration chamber 42. The calibration output signal on line 41 at frequency $2f_o$ is representative of the degree of absorption by calibration chamber 42 of the incident radiation beam 43, the energy loss in sample chamber 12 being negligible.

Radiation beam 43 produces a pressure wave within calibration chamber 42 detected by microphone 46 to produce a signal on line 47 which is amplified by amplifier 48 to provide a signal on line 53 for comparison with the signal from frequency doubler 28 in phase sensitive detector 52 to provide the calibration signal on line 41.

The signal on line 47 at frequency $f_o$ may be detected by phase sensitive detector 57 to provide an error signal representative of the displacement of the center of the absorption maximum from the center of the wavelength range for application to phaselocked loop 58 to lock the center frequency of radiation beam 13 to the center of the absorption spectrum. The remainder of the system shown in FIG. 5 operates as described above in the discussion of FIG. 1.

The ratio R, $$R = \frac{\text{sample signal (Line 11)}}{\text{calibration signal (Line 41)}} \tag{15}$$

will be accurately related to the concentration of absorbing species in the sample chamber, and insensitive to changes in the operating parameters $f_o$, $\epsilon$, and the intensity of the radiation beam. In the limit of small absorption, as with the detection of atmospheric pollutants, R is equal to the concentration of species "A" in the sample chamber divided by the concentration of species "A" in the calibration chamber.

Referring to FIG. 5, the calibration chamber 42 is depicted as being optically in series with the sample chamber 12, an optically transparent medium at wavelength $\nu_a$ being interposed between the two. It is also possible, without compromise of the desirable features of the invention, to operate cells 12 and 42 optically in parallel. For this purpose, radiation beam 13 is divided by suitable means such as a beamsplitter such that a portion of beam 13 is incident on each of the aforementioned cells.

Figure 6:
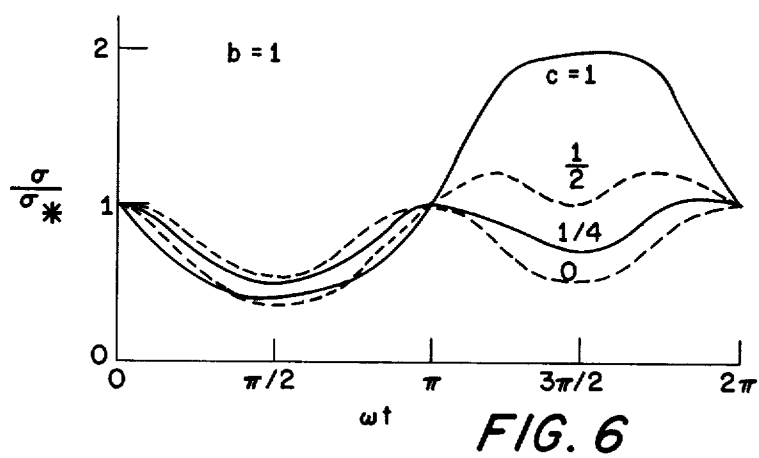
FIG. 6 is a graphical representation of normalized absorption as a function of $\omega t$ for $b = 1$.

Use of the calibration chamber to adjust and stabilize the wavelength of the radiation source is illustrated by reference to FIG. 6, which depicts the change in $(\sigma/\sigma_o)$ which occurs as the frequency offset parameter, $c$, varies. It is apparent that the spectral content of the microphone signal will vary rapidly as $c$ varies. When $c = 0$, Eq. (5) demonstrates that there is no signal component at $f_o$, but a substantial component at $2f_o$. Conversely, when $c$ becomes large, Eq. (7) demonstrates that the $f_o$ component is large compared to that at $2f_o$. Consequently, the ratio of the signals on line 47 at $f_o$ and $2f_o$ may be used to drive phase-locked loop 58 for controlling the source wavelength $\nu_a$. It is important to note that the ratio $$G = \frac{\text{Signal at } 2f_o}{\text{Signal at } f_o} \tag{16}$$

on signal line 47 increases to a maximum at $c = 0$, and decreases monotonically as $c$ increases. This is very desirable for setting $\nu_a$ at a specified value relative to the line center $\nu_o$.

Figure 4:
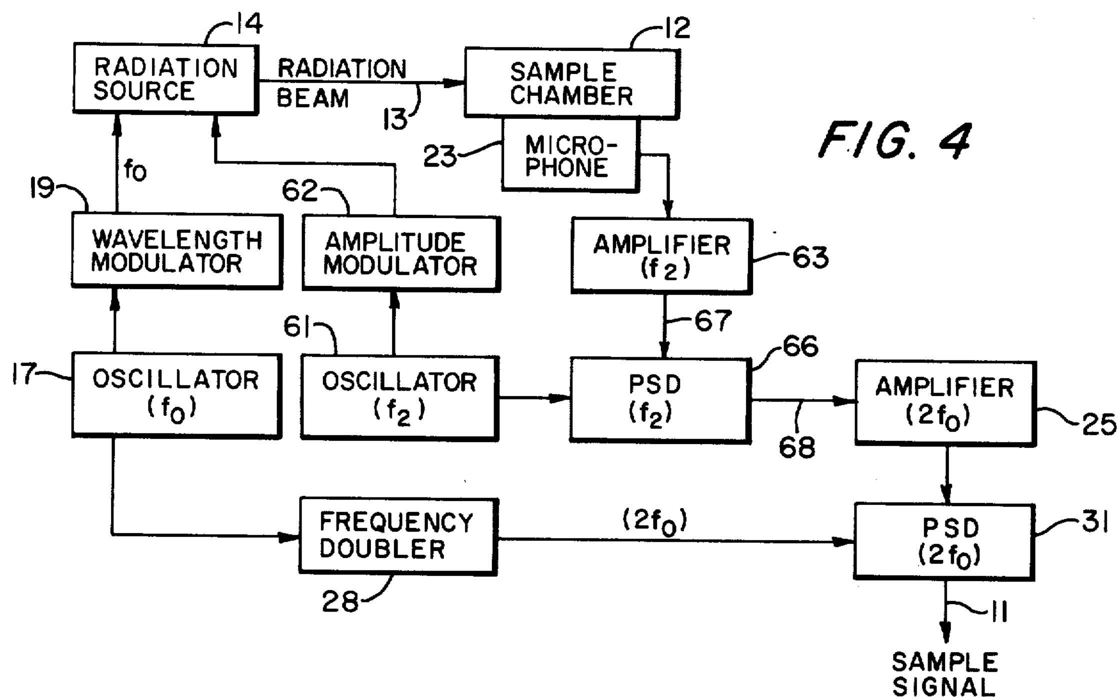
FIGS. 4 and 5 are block diagrams illustrating the logical arrangement of embodiments according to the invention.

It is within the principles of the invention to adapt the apparatus of FIG. 4 to include a calibration chamber as in FIG. 5. Also amplifier 48 and phase sensitive detector 52 in FIG. 5 may be eliminated and amplifier 25 and phase sensitive detector 31 of the sample chamber periodically connected to calibration chamber 42 for calibration purposes. An analog sample-and-hold amplifier or a digital memory may store the calibration signal between calibrations. This method is particularly useful when further processing of the sample signal is to be performed.

It is also within the principles of the invention to use sample cell 12 for calibration purposes. This is accomplished by introducing a gas sample containing a known concentration of species A into the cell 12 to obtain a signal on line 11 corresponding to the calibration signal on line 41 and to adjust the central wavelength $\nu_a$ to achieve the appropriate value of G, Eq. (16), using the signals at $f_o$ and $2f_o$ on line 24.

Many suitable radiation sources are known to the art. Laser sources whose wavelengths can be varied are particularly desirable because the sample signal is proportional to the intensity of the radiation beam. Among the known lasers which are suitable would be: dye lasers, particularly in the 3,200A- 11,000A region of the spectrum; spin-flip Raman lasers; semiconductor lasers which may be temperature tuned and pressure tuned, or tuned by the action of a magnetic field; high-pressure gas lasers such as $CO_2$ lasers; low-pressure gas lasers whose wavelength may be varied by the Zeeman effect; circumstances in which the *absorbing line of the gas* (rather than the wavelength of the source) may be tuned by the Zeeman effect (e.g. NO measured using a CO laser), and tunable lasers, such as dye lasers, whose wavelength has been shifted to other regions of the spectrum by nonlinear optical effects (e.g. frequency doubling, difference frequency generation, Raman shifting, etc.). In addition to laser sources, thermal sources such as black bodies and flashlamps may also be useful in certain regions of the spectrum. Tuning of these sources can be accomplished using dispersive elements (gratings, prisms, etc.) and by interference elements (e.g. Fabry-Perot etalons, narrowband interference filters, etc.).

There has been described novel apparatus and techniques for opto-acoustic spectroscopy characterized by sectional isolation of system error and noise and numerous other features. It is evident that those skilled in the art may now make numerous uses and modifications of and departures from the specific embodiments described herein without departing from the inventive concept. Consequently, the invention is to be construed as embracing each and every novel feature and novel combination of features present or in possessed by the apparatus and techniques herein disclosed and limited solely by the spirit and scope of the appended claims.

What is claimed is:

1. Apparatus for detecting the presence of a species in a medium comprising,
   - means defining a sample chamber for receiving said medium,
   - a source of a beam of radiant energy incident upon said sample chamber for producing pressure waves therein of intensity related to the degree of absorption by said medium,
   - means modulating the wavelength of said radiant energy through a wavelength range including a spectral line characteristic of said species at a rate corresponding to a wavelength modulation frequency,
   - and first acoustical detecting means for detecting the intensities of individual frequency components of said pressure wave signals produced in said sample chamber to provide an output signal representative of the degree of absorption of the medium in said sample chamber.

2. Apparatus for detecting the presence of a species in a medium in accordance with claim 1 wherein said pressure wave signals are detected at a frequency substantially double said wavelength modulation frequency.

3. Apparatus for detecting the presence of a species in a medium in accordance with claim 1 and further comprising,
   - means defining a calibration chamber for energization by said beam of radiant energy to produce calibration pressure waves therein,
   - second acoustical detecting means for detecting said calibration pressure waves to provide an output calibration signal,
   - and means responsive to said calibration signal for reducing errors in said output signal.

4. Apparatus for detecting the presence of a species in a medium in accordance with claim 3 and further comprising means for adjusting the center of said wavelength range to achieve a desired relation to the center of the spectral characteristic of said species.

5. Apparatus for detecting the presence of a species in a medium in accordance with claim 4 wherein said means for adjusting comprises a phase-locked loop.

6. Apparatus for detecting the presence of a species in a medium in accordance with claim 1 wherein said source is a wavelength tunable laser.

7. Apparatus for detecting the presence of a species in a medium in accordance with claim 1 and further comprising means for modulating the intensity of said beam at a rate corresponding to a predetermined intensity modulation frequency substantially equal to a resonant frequency of said means defining a sample chamber.

8. Apparatus for detecting the presence of a species in a medium in accordance with claim 7 wherein said wavelength modulation frequency is separated substantially from said intensity modulation frequency.

9. Apparatus for detecting the presence of a species in a medium in accordance with claim 7 wherein said wavelength modulation frequency is smaller than one half the inverse of the acoustic response time of said sample chamber.

10. Apparatus for detecting the presence of a species in a medium in accordance with claim 3 and further means for modulating the intensity of said beam at a rate corresponding to a predetermined intensity modulation frequency substantially equal to a resonant frequency of said means defining a sample chamber and said means defining a calibration chamber.

11. Apparatus for detecting the presence of a species in a medium in accordance with claim 7 wherein,
   - said source comprises a wavelength tunable laser,
   - said wavelength modulation frequency is separated substantially from said intensity modulating frequency and less than one half the inverse of the acoustic response time of said sample chamber.

12. Apparatus for detecting the presence of a species in a medium in accordance with claim 1 said pressure wave signals are detected at frequencies corresponding substantially to the fundamental, second harmonic and third harmonic of said wavelength modulation frequency,
   - and means for utilizing the pressure wave signals detected at said first and third harmonics for more accurately determining the pressure wave signal component at said second harmonic of said wavelength modulation frequency.

13. Apparatus for detecting the presence of a species in a medium in accordance with claim 12 and further comprising,
   - means for determining the ratio between signal at said third harmonic and signal at said fundamental,
   - and means for determining the ratio between signal at said second harmonic and signal at said fundamental.

14. A method of detecting the presence of a species in a medium which method includes the steps of, introducing said medium into a sample chamber, exciting said medium with a beam of radiant energy wavelength modulated through a wavelength range including a spectral line characteristic of said species at a rate corresponding to a wavelength modulation frequency to produce pressure waves in said sample chamber, and detecting the intensities of individual frequency components of said pressure waves to provide an output signal representative of the degree of absorption of said medium in said sample chamber.

15. A method in accordance with claim 14 and further including the steps of adjusting the center of said range to achieve a desired relation to the center of the spectral characteristic of said species.

16. A method in accordance with claim 14 and further including the step of modulating the intensity of said beam at a rate corresponding to a predetermined intensity modulation frequency substantially equal to a resonant frequency of said sample chamber.

* * * * *